United States Patent [19]

Telle et al.

[11] Patent Number: 4,670,882

[45] Date of Patent: Jun. 2, 1987

[54] DYESTUFF LASER

[75] Inventors: Helmut Telle, Cologne; Rudolf Schieder, Huerth; Roderich Raue, Leverkusen; Udo Eckstein, Cologne, all of Fed. Rep. of Germany

[73] Assignee: Bayer Aktiengesellschaft, Leverkusen, Fed. Rep. of Germany

[21] Appl. No.: 349,900

[22] Filed: Feb. 18, 1982

Related U.S. Application Data

[63] Continuation of Ser. No. 077,446, Sep. 20, 1979, abandoned.

[30] Foreign Application Priority Data

Oct. 7, 1978 [DE] Fed. Rep. of Germany ....... 2843850

[51] Int. Cl.$^4$ ................................................. H01S 3/20
[52] U.S. Cl. .................................. 372/53; 252/301.17; 252/301.32
[58] Field of Search .................... 372/53; 252/301.17, 252/301.32

[56] References Cited

U.S. PATENT DOCUMENTS 3,859,350  1/1975  Sahm et al. .................... 252/301.32

OTHER PUBLICATIONS

Majewski et al., Optics Communications, Aug. 1976, pp. 255–259.

*Primary Examiner*—William D. Larkins

*Attorney, Agent, or Firm*—Sprung Horn Kramer & Woods

[57] ABSTRACT

Dyestuff laser consisting of a reservoir, with a laser dyestuff solution contained therein, and a pumped light source associated therewith, which is capable of exciting the dyestuff solution to produce an emission, characterized in that the dyestuff solution contains, in a solvent which does not interfere with the emission, a dyestuff which, in the form of the free acid, corresponds to the general formula

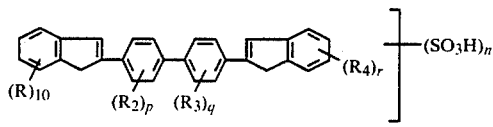

wherein
$R_1$ to $R_4$ independently of one another represent hydrogen, alkyl, trifluormethyl, alkoxy, aralkoxy, alkenyloxy, halogen or the carboxyl, cyano, alkylsulphone, aryl-sulphone, carboxamide, sulphonamide or carboxylic acid ester group,
$R_1$ and $R_4$ can additionally denote a fused-on benzene ring,
n represents a number 2 to 6 and
o, p, q and r independently of one another represent 0, 1 or 2, in a concentration, preferably of $10^{-2}$ to $10^{-5}$ mol/l, which emits laser radiation.

7 Claims, 4 Drawing Figures

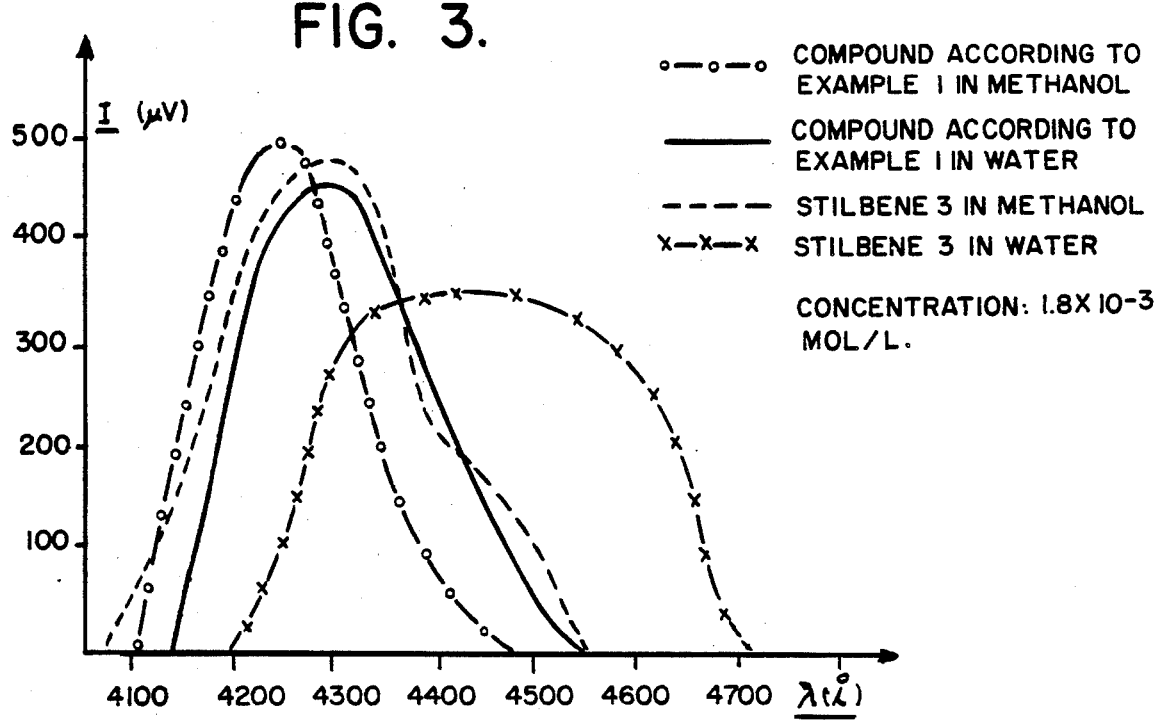
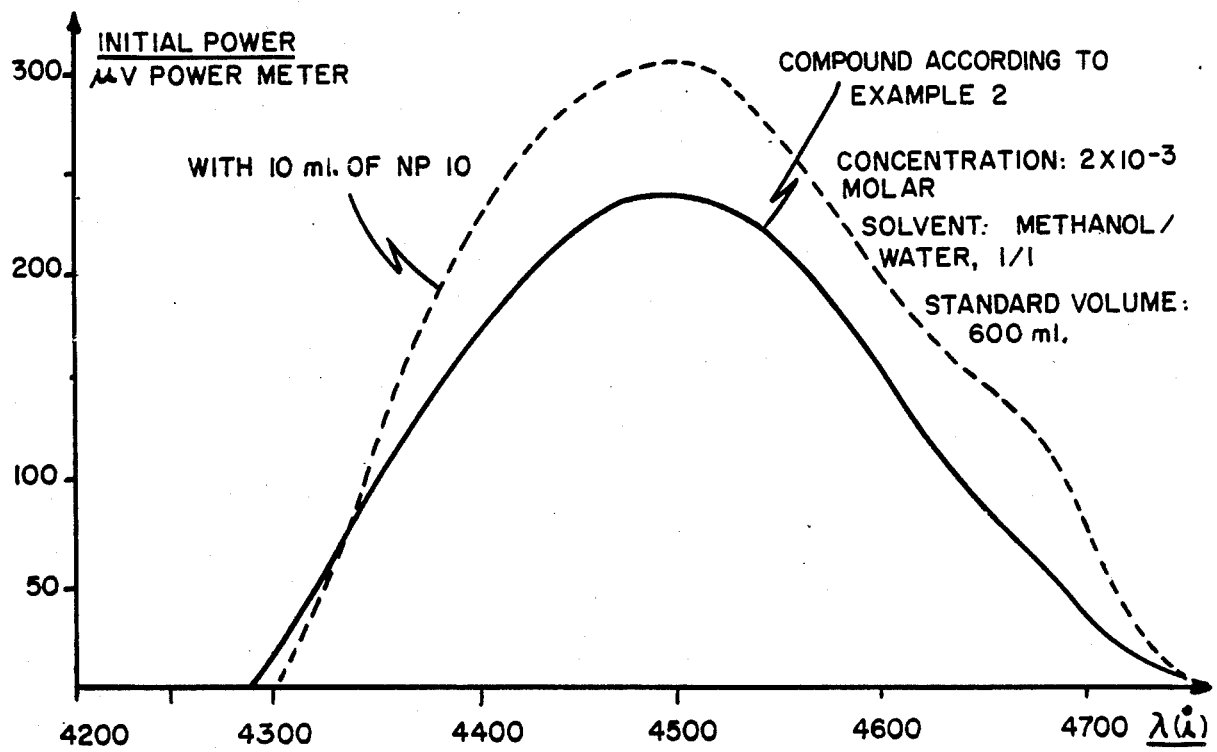

DYESTUFF LASER

This is continuation of application Ser. No. 77,446, filed Sept. 20, 1979, now abandoned.

BACKGROUND OF THE INVENTION

1. Field of the Invention

The invention relates to a process for the production of coherent monochromatic radiation (laser light), the frequency of which can be changed, by means of a dyestuff laser which consists of a reservoir for the dyestuff solution and an energy source, associated therewith, which is capable of exciting the dyestuff solution to produce an emission, the radiation produced being in the wavelength range of 420 to 480 nm.

2. Discussion of Prior Art

A laser is a light amplification device by means of which it is possible to produce coherent monochromatic light of a high spectral and geometric intensity density. The laser consists of an optical resonator which contains the liquid laser-active material in a thin-walled quartz cell. The cell is usually part of a closed system through which the dyestuff solution is circulated by pumping whilst the laser is in operation. The active medium can also be in the form of a liquid jet, which issues from a nozzle perpendicular to the optical axis and transverses the resonator. Local overheating, which would lead to optical inhomogeneities, is avoided in both arrangements.

The excitation of the dyestuffs is effected with the aid of energy sources, by means of electrons or light, and the dyestuff laser can also be excited by a gas laser, for example a nitrogen laser, argon laser or krypton laser.

The excitation, which is also termed optical pumping, has the effect of raising the electrons of the molecule of the laser dyestuff from their normal state to a higher energy state, from which a radiation transition takes place. If the number of molecules in the excited state exceeds that of the molecules in lower states, this gives rise to stimulated transitions, by means of which the light is amplified in the optical resonator.

If one of the laser mirrors is particlally transparent to light, a part of the radiation leaves the apparatus in the form of a laser beam. Dyestuffs which can be excited particularly easily exhibit the phenomenon of "super radiance" with highly effective excitation. This can be observed, for example, if a quartz cell containing the solution of such a dyestuff is placed in the beam of a nitrogen laser. The solution then emits light in a preferred direction, similarly to the case of a laser, without being located between resonator mirrors.

A considerable advantage of the dyestuff laser compared with a solid laser or gas laser is its ability to supply laser radiation of a frequency which can be changed. Because of the width of the fluorescence band of the dyestuffs employed, dyestuff lasers can be so tuned, by inserting a frequency-selective element, for example a reflection grating, prism or doubly refracting filter, that laser light is emitted at any desired wavelength within the entire flourescence band of the dyestuff.

Although a large number of suitable dyestuffs have already been proposed, there is, nevertheless, still a considerable lack, in many regions of the visible wavelength range, of compounds which give a very high degree of effectiveness of the laser.

SUMMARY OF THE INVENTION

The invention accordingly relates to a dyestuff laser consisting of a reservoir, with a laser dyestuff solution contained therein, and a pumped light source associated therewith, which is capable of exciting the dyestuff solution to produce an emission, characterised in that the dyestuff solution contains, in a solvent which does not interfere with the emission, a dyestuff which, in the form of the free acid, corresponds to the general formula

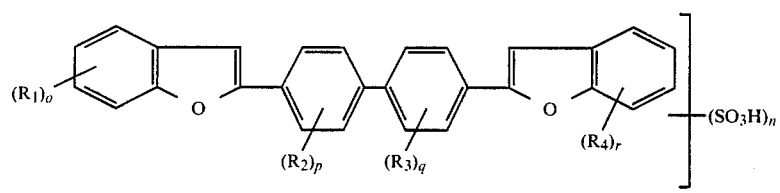

wherein
$R_1$ to $R_4$ independently of one another represent hydrogen, alkyl, trifluoromethyl, alkoxy, aralkoxy, alkenyloxy, halogen or the carboxyl, cyano, alklsulphone, aryl-sulphone, carboxamide, sulphonamide or carboxylic acid ester group,
$R_1$ and $R_4$ can additionally denote a fused-on benzene ring,
n represents a number from 2 to 6 and
o, p, q and r independently of one another represent 0, 1 or 2,
in a concentration, preferably of $10^{-2}$ to $10^{-5}$ mol/l, which emits laser radiation.

DESCRIPTION OF SPECIFIC EMBODIMENTS

Examples of substituents of the aromatic radicals which may be mentioned are: $C_1$- to $C_5$-alkyl radicals, which can be further substituted by hydroxyl, cyano, halogen or phenyl, such as methyl, ethyl, cyanoethyl and tert.-butyl; benzyl; halogen atoms, such as chlorine, bromine or fluorine, preferably chlorine; $C_1$- to $C_5$-alkoxy radicals, such as methoxy, ethoxy, butoxy and isopropoxy; allyloxy; benzyloxy; $C_1$- to $C_5$-alkylsulphonyl radicals which are optionally further substituted by hydroxyl, such as methylsulphonyl, ethylsulphonyl, n-butylsulphonyl and β-hydroxyethylsulphonyl; the benzylsulphonyl radical; the phenylsulphonyl radical; carboxamide or sulphonamide groups which are optionally monosubstituted or disubstituted by $C_1$- to $C_4$-alkyl radicals; cyano; and carboxylic acid $C_1$- to $C_4$- alkyl ester groups.

In the case where the dyestuffs which can be used according to the invention are in the form of salts, possible salt-forming cations are monovalent or divalent metals, such as sodium, potassium, lithium, magnesium, calcium, barium, manganese and zinc, and ammonium salts and substitution products thereof, which are obtained by reacting the acids on which they are based with mono-, di- or tri- methylamine, mono-, di- or tri ethylamine, mono-, di- or tri-ethanolamine, methyldiethanolamine, ethyldiethanolamine, dimethylethanolamine, diethylethanolamine, mono-, di- or tri-isopropanolamine, methyldiisopropanolamine, ethyldiisopropanolamine, dimethylisopropanolamine, n-butylamine, sec.-butylamine, dibutylamine, diisobutylamine, trishydroxyethoxyethylamine, pyridine, morpholine or piperidine.

Preferred compounds corresponds, in the form of the free acid, to the formula

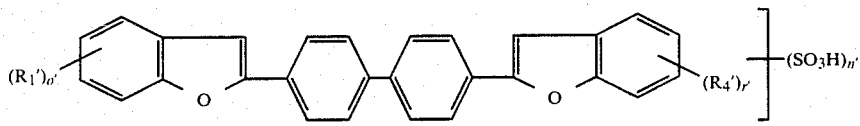

wherein
the radicals $R_1'$ and $R_4'$ independently of one another represent $C_1$- to $C_4$-alkyl, $C_1$- to $C_4$-alkoxy, benzyloxy, phenoxy, cyano, halogen, a carboxyl, carboxylic acid ester or carboxamide group or a fused-on benzene ring.
$n'$ denotes 2, 3 or 4 and
$o'$ and $r'$ independently of one another denote 0 or 1.
The use of a compound of the formula

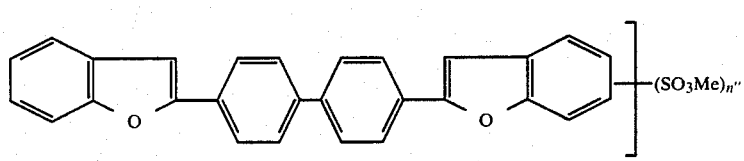

in which
Me represents hydrogen, sodium, potassium or an optionally substituted ammonium radical and
$n''$ denotes 2, 3 or 4,
as a laser dyestuff is of particular importance.

Examples of solvents which do not interfere with the stimulated emission and which can be used according to the invention are: water; monohydric and polyhydric alcohols, for example methanol, ethanol, isopropanol, butanol and ethylene glycol; glycol monomethyl ether; cyclic ethers, such as tetrahydrofurane and dioxane; esters, such as glycol diacetate and diethyl carbonate; fluorinated alcohols, for example hexafluoroisopropanol; and lower aliphatic amides, such as dimethylformamide and diethylformamide.

It is equally possible to use solvent mixtures, especially mixtures of alcohols with water.

In water, a number of the compounds according to the invention display a reduction in the laser activity as a result of association. In this case, the laser activity can be increased by adding surface-active compounds, especially non-ionic emulsifiers, for example the reaction products of $C_9$- to $C_{12}$-alkylphenols, phenylalkylphenols, hydroxydiphenyl, oleyl alcohol or longer-chain aliphatic alcohols and 6 to 50 mols of ethylene oxide.

In recent years, laser light from lasers which have a frequency which can be changed has attained considerable importance in spectroscopy. The lasers can be employed for analytical purposes, high-resolution spectroscopy, fluorescence spectroscopy, absorption spectroscopy, life measurements and photoionisation and in the spectroscopy of negative ions. They are also of great technical importance in information techniques, in environmental protection and for the separation of isotopes.

The compounds according to the invention are suitable for use in the short-wave range of the visible spectrum and, when used in a dyestuff laser, are distinguished by an exceptionally high stability to light.

The compounds according to the invention are prepared in a known manner by reacting 4,4'-biphenylene-bis-(methylenoxy-2-benzaldehydes) or bis-anils thereof in dipolar aprotic solvents, with the addition of strongly basic alkali metal compounds, to give the benzofuranes and subsequent sulphonation of these products in accordance with the method of German Offenlegungsschriften Nos. 2,238,628 and 2,361,338.

BRIEF DESCRIPTION OF DRAWINGS

Referring to the drawings herein:

FIG. 3, is a graph similar to FIG. 2, showing the interrelationship of initial power to wavelength of a dyestuff according to Example 1 in various solvents and comparing the same to Stilbene 3 in the same solvent; and FIG. 4, is a graph similar to FIGS. 2 and 3, showing the interrelationship of initial power to wavelength of a compound according to Example 2.

EXAMPLE 1

The compound of the formula

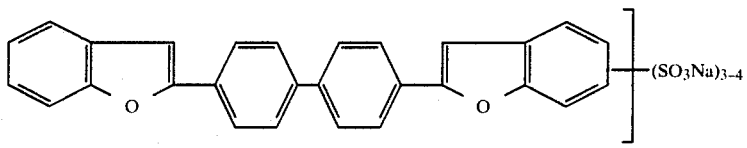

Figure 1:
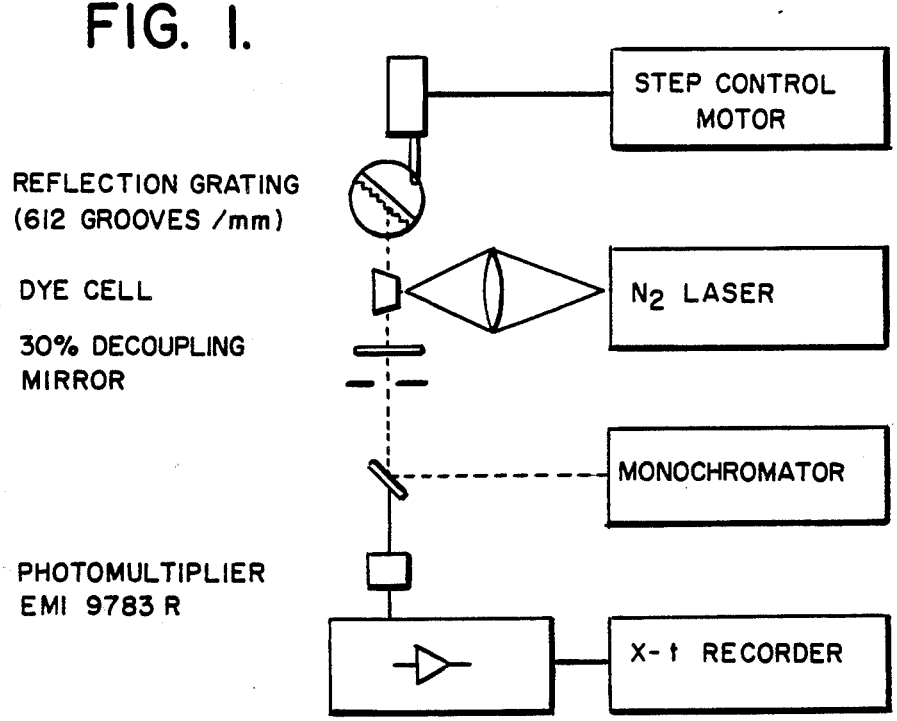
FIG. 1, shows diagrammatically an apparatus for measuring the laser spectrum via a photomultiplier provided by the use of a dyestuff laser of the invention.

was dissolved in methanol in a concentration of $1.9 \times 10^{-3}$ mol/l. In an apparatus according to FIG. 1, this solution was pumped from a reservoir through the dyestuff cell. The frequency of the wavelength was varied by a reflection grating with a step motor drive. The laser spectrum was recorded via a photomultiplier, which was spectrally calibrated, and the wavelength was calibrated via a monochromator. In order to measure the power, the photomultiplier was replaced by a thermopile measuring head with an ancillary measuring amplifier. The intensity in percent of the pump power is also given in kW, since the initial pulse power was 100 kW.

The nitrogen laser used had a wavelength of 337 nm, a pulse frequency of 100 Hz, a pulse width of 7 nseconds and a pulse peak power of 100 kW.

Figure 2:
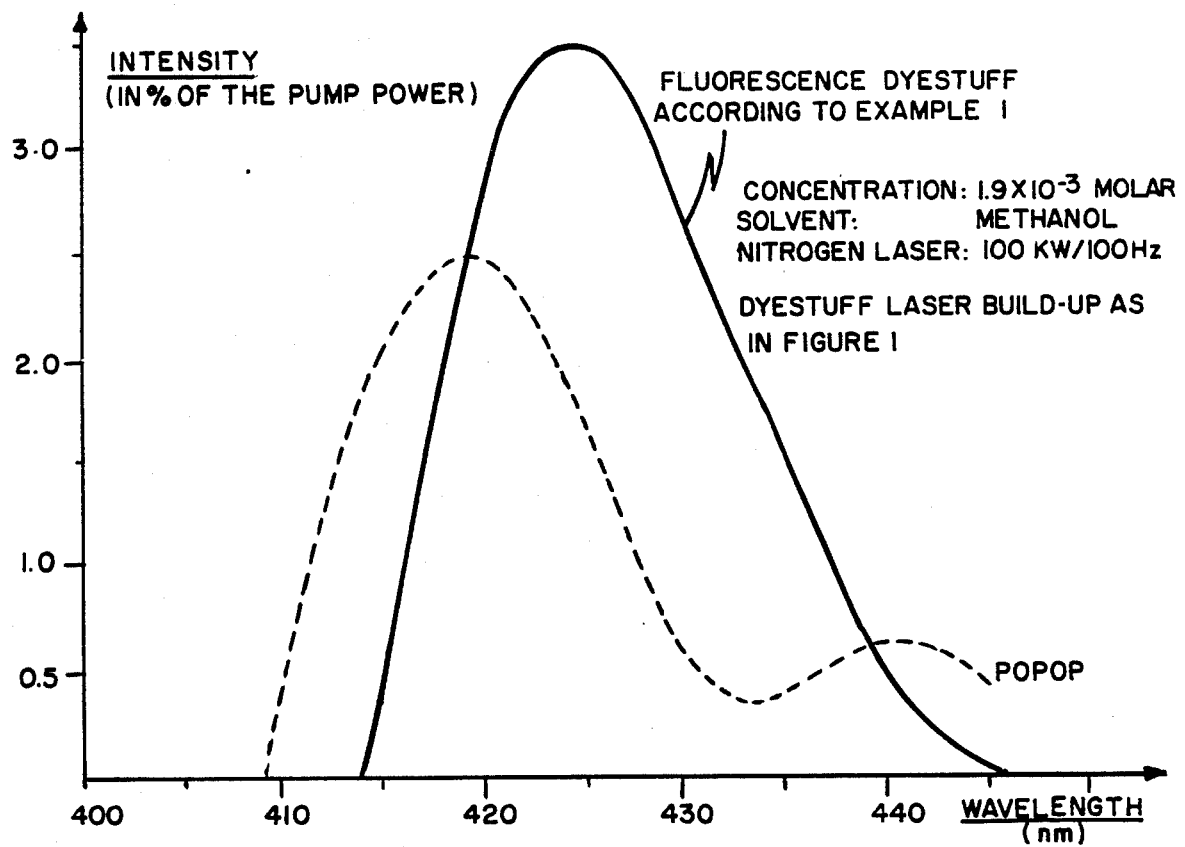
FIG. 2, is a graph which plots the intensity against wavelengths provided by a fluorescent dyestuff according to Example 1, and provided by the known dyestuff (1,4-bis-[2-5(-phenyloxazolyl)]-benzene), known as POPOP.

The dependence of the laser power on the wavelength is given in FIG. 2. The known laser dyestuff POPOP (1,4-bis-[2-(5-phenyloxazolyl)]-benzene), the laser activity of which is described in Optics Communications 24,1—page 33 (January 1978), was used as the comparison substance. The compound according to the invention shows a higher initial power over a wider spectral range.

Compared with the known laser dyestuff Stilbene 3, the laser activity of which is described in Optics Communications 23,3—page 251 (March 1978), the compound according to the invention has the advantage that it provides virtually the same initial power in water and in methanol, whilst Stilbene 3 has a greatly reduced maximum at longer wavelengths in water. This is illustrated in FIG. 3.

EXAMPLE 2

The compound of the formula

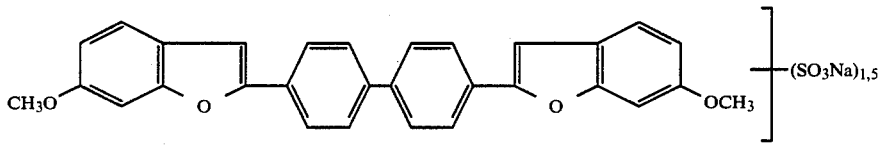

was dissolved in a mixture of 50% of methanol and 50% of water in a concentration of $2 \times 10^{-3}$ mol/l. The laser activity of the compound was investigated in the same apparatus and by the same procedure as in Example 1. The laser power curve is extended considerably into the region of long wavelength, and the initial power was increased significantly by adding 1% of the reaction product of nonylphenol and 10 mols of ethylene oxide. This can be seen from FIG. 4.

The compound used in this example was obtained in the following manner:

83.7 g of 4-methoxysalicylaldehyde are added in portions to a suspension of 31 g of Na methylate in 250 ml of dimethylformamide at 60° C. The mixture is stirred at 80° C. for 1 hour, a little potassium iodide is added and a solution of 62.75 g of bischloromethylbiphenyl in 200 ml of dimethylformamide is then added dropwise in the course of 1 hour. The mixture is stirred at the boiling point for 3 hours and the solvent is distilled off under a water pump vacum. The reaction mixture is then cooled to 0° C. and 300 ml of a 1/1 mixture of water and methanol are added. The mixture is neutralised with concentrated hydrochloric acid and stirred at 0° C. for 1 hour and the intermediate product is filtered off. After washing with water and drying in vacuo, 105 g (=87% of theory) of yellow crystals of melting point 135°–140° C. are obtained.

33.8 g of the compound thus prepared, of the formula

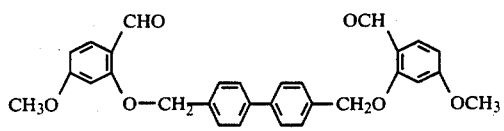

are dissolved in 400 ml of dimethylformamide under a nitrogen atmosphere. 19.6 g of potassium tert.-butylate are added in portions at 80°–100° C. in the course of 1 hour, whilst irradiating the mixture with a 500 W lamp. The reaction mixture is subsequently stirred at 100°–120° C. for a further 2 hours, cooled to 0°–5° C. and then neutralised to pH 7 with acetic acid. The compound of the formula

is filtered off, washed with water and then with methanol and dried in vacuo. 15 g (=48% of theory) of a yellow crystalline powder with a melting point above 300° C. are obtained.

10 g of chlorosulphonic acid, dissolved in 20 ml of o-dichlorobenzene, are added dropwise to 8.93 g of this compound in 150 ml of anhydrous dichlorobenzene at 0°–5° C., whilst cooling with ice. The mixture is then stirred at 0°–5° C. for 5 hours and at room temperature for 15 hours. The reaction mixture is then poured onto 300 ml of ice-water and neutralised with sodium hydroxide solution and the organic phase is separated off. Active charcoal is added to the aqueous phase and the mixture is heated to the boiling point and filtered. Salting out with sodium chloride gives 21 g of the compound according to the invention with a sodium chloride content of 13.4%.

The following compounds can be used in dyestuff laser apparatuses in the same manner:

What is claimed is:

1. Dyestuff laser consisting of a reservoir, with a laser dyestuff solution contained therein, and a pumped light source associated therewith, which is capable of exciting the dyestuff solution to produce an emission, characterised in that the dyestuff solution contains, in a solvent which does not interfere with the emission, a dyestuff which, in the form of the free acid, corresponds to the general formula

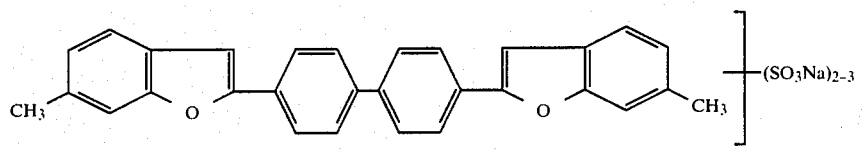

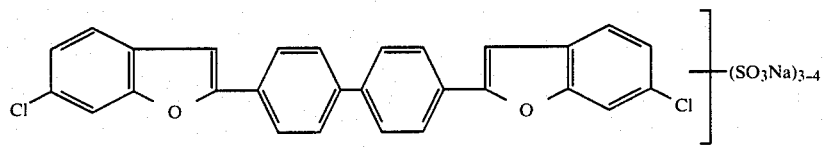

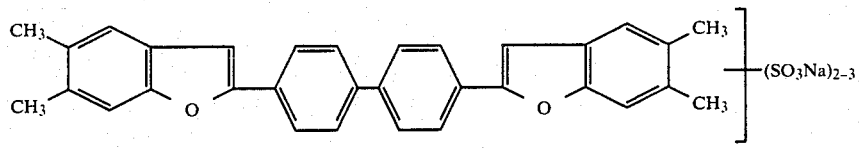

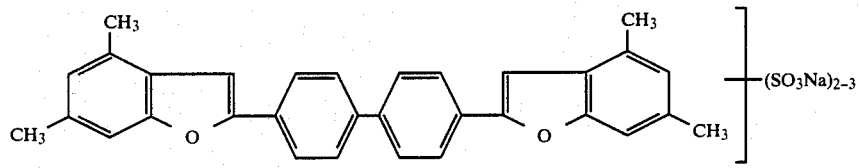

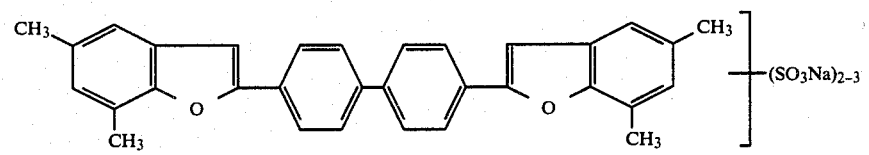

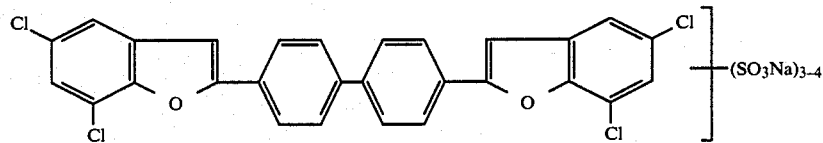

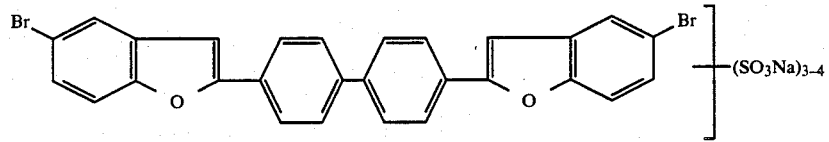

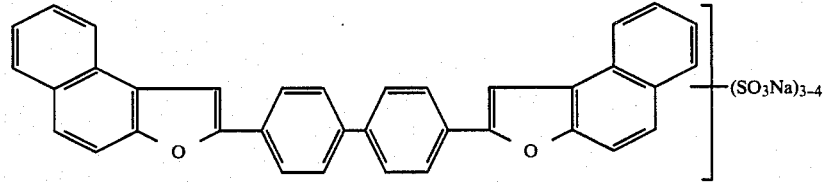

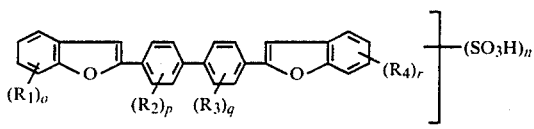

wherein

R₁ to R₄ independently of one another represent hydrogen, alkyl, trifluoromethyl, alkoxy, aralkoxy, alkenyloxy, halogen or the carboxyl, cyano, alkylsulphone, aryl-sulphone, carboxamide, sulphonamide or carboxylic acid ester group, R₁ and R₄ can additionally denote a fused-on benzene ring, n represents a number from 2 to 6 and o, p, q and r independently of one another represent 0, 1 or 2, in a concentration which emits laser radiation.

2. Dyestuff laser consisting of a reservoir, with a laser dyestuff solution contained therein, and a pumped light source associated therewith, which is capable of exciting the dyestuff solution to produce an emission, characterised in that the dyestuff solution contains, in a solvent which does not interfere with the emission, a dyestuff which, in the form of the free acid, corresponds to the general formula

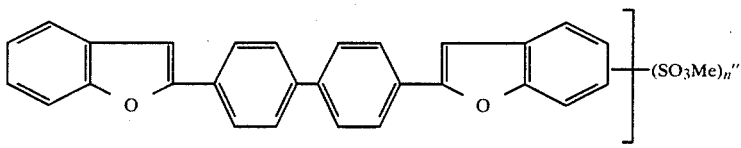

wherein the radicals R₁' and R₄' independently of one another represent C₁- to C₄-alkyl, C₁- to C₄-alkoxy, benzyloxy, phenoxy, cyano, halogen, a carboxyl, carboxylic acid ester or carboxamide group or a fused-on benzene ring, n' denotes 2, 3 or 4 and o' and r' independently of one another denote 0 or 1, in a concentration which emits laser radiation.

3. Dyestuff laser consisting of a reservoir, with a laser dyestuff solution contained therein, and a pumped light source associated therewith, which is capable of exciting the dyestuff solution to produce an emission, characterised in that the dyestuff solution contains, in a solvent which does not interfere with the emission, a dyestuff of the general formula

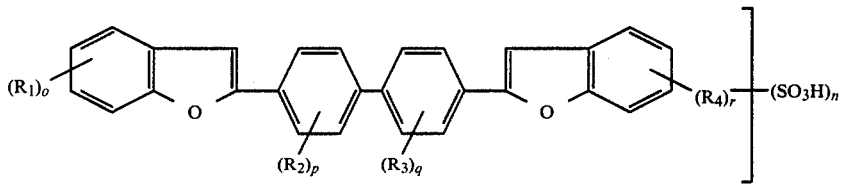

in which

Me represents hydrogen, sodium, potassium or an optionally substituted ammonium radical and n'' denotes 2, 3 or 4, in a concentration which emits laser radiation.

4. A process for the production of a coherent laser emission in a wavelength range of 420–480 nm which comprises pumping light from a light source into a reservoir containing a laser dyestuff solution, said solution comprising a solvent which does not interfere with laser emission and dyestuff which, in the form of a free acid, corresponds to the general formula

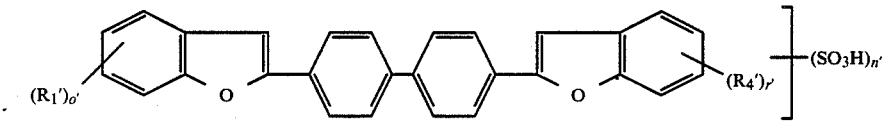

wherein

R₁ to R₄ independently of one another represent hydrogen, alkyl, trifluoromethyl, alkoxy, aralkoxy, alkenyloxy, halogen or the carboxyl, cyano, alkylsulphone, aryl-sulphone, carboxamide, sulphonamide or carboxylic acid ester group, R₁ and R₄ can additionally denote a fused-on benzene ring, n represents a number from 2 to 6 and o, p, q and r independently of one another represent 0, 1 or 2, in a concentration which emits laser emission.

5. A process according to claim 4, wherein said dyestuff has the formula

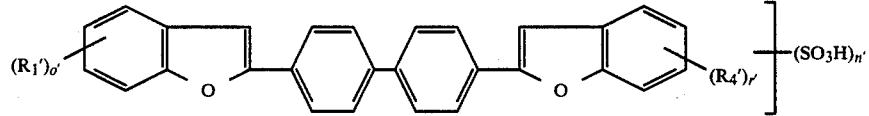

wherein
the radicals $R_1'$ and $R_4'$ independently of one another represent $C_1$-$C_4$-alkyl, $C_1$- to $C_4$-alkoxy, benzyloxy, phenoxy, cyano, halogen, a carboxyl, carboxylic acid ester or carboxamide group or a fused-on benzene ring,
n′ denotes 2, 3 or 4 and
o′ and r′ independently of one another denote 0 or 1.

6. A process according to claim 4, wherein said dyestuff has the formula

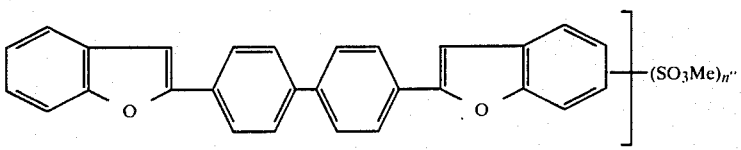

in which
Me represents hydrogen, sodium potssium or an optionally substituted ammonium radical and
n″ denotes 2, 3 or 4.

7. A dyestuff laser according to claim 1, wherein said dyestuff is present in said solution in a concentration of $10^{-2}$ to $10^{-5}$ mol/l.

* * * * *